United States Patent [19]
Jones

[11] Patent Number: 5,605,148
[45] Date of Patent: Feb. 25, 1997

[54] GAS MIXING DEVICES FOR RESUSCITATION/LUNG VENTILATION APPARATUS

[75] Inventor: Norman S. Jones, Leighton Buzzard, United Kingdom

[73] Assignee: pneuPAC Limited, Bedfordshire, United Kingdom

[21] Appl. No.: 496,251

[22] Filed: Jun. 28, 1995

[30] Foreign Application Priority Data

Sep. 5, 1994 [GB] United Kingdom .................. 9413499

[51] Int. Cl.$^6$ ................................................ A61M 16/12
[52] U.S. Cl. ................................ 128/205.11; 128/203.12; 128/203.25
[58] Field of Search .................. 128/203.12, 203.25, 128/204.25, 205.11, 207.18

[56] References Cited

U.S. PATENT DOCUMENTS

| | | | |
|---|---|---|---|
| 3,794,072 | 2/1974 | Diedrich et al. | 137/893 |
| 3,913,607 | 10/1975 | Price | 137/271 |
| 4,036,253 | 7/1977 | Fegan et al. | 137/556 |
| 4,682,591 | 7/1987 | Jones | 128/204.25 |
| 4,848,333 | 7/1989 | Waite | 128/205.11 |

FOREIGN PATENT DOCUMENTS

| | | |
|---|---|---|
| 0342883 | 11/1989 | European Pat. Off. . |
| 2174760 | 11/1986 | United Kingdom . |
| 2174609 | 11/1986 | United Kingdom . |

*Primary Examiner*—V. Miller
*Assistant Examiner*—Eric P. Raciti
*Attorney, Agent, or Firm*—Arnold B. Silverman; Alan G. Towner; Eckert Seamans Cherin & Mellott

[57] ABSTRACT

A resuscitation/ventilation apparatus incorporates an entrainment mixer with a nozzle, discharging entraining gas into an entrainment chamber, the nozzle being connected with a high pressure source of the entraining gas. One entrainment port to the entrainment chamber is connected to atmosphere and another entrainment port is connected to an oxygen source. A continuously variable restriction is disposed in the oxygen supply conduit upstream of the other entrainment port and is variable independently of any control of the entraining gas supply, to enable delivery of a gas mixture of steplessly variable oxygen concentration.

7 Claims, 3 Drawing Sheets

GAS MIXING DEVICES FOR RESUSCITATION/LUNG VENTILATION APPARATUS

FIELD OF THE INVENTION

THIS INVENTION concerns resuscitation/lung ventilation apparatus of the type adapted to deliver pulses of breathable gas to the respiratory passages of a patient to accomplish forced ventilation of the lungs in cases of respiratory failure or impairment. The invention is more especially concerned with gas mixing devices that may be incorporated in such apparatus to enable the output of a gas mixture by apparatus powered by a pressurised breathable gas such as compressed air or oxygen.

Although of general applicability to resuscitation/ventilation apparatus, the invention is especially applicable to portable apparatus such as may be used by emergency services for resuscitation and short-term ventilation purposes. Such portable apparatus is almost invariably designed to deliver pulses of pure oxygen from a compressed oxygen source because not only is pure oxygen ventilation beneficial for short term application such as in resuscitation, but the use of compressed oxygen to power the apparatus enables the latter to employ very simple and robust control and valve devices, resistant to abuse and easily operated correctly by personnel with a minimum of training. Indeed, these features of such apparatus have led to its increasing use for longer term ventilation, as when patients with impaired respiratory function are subject to extended transportation. However, because long-term ventilation with pure oxygen is not always beneficial to a patient and, moreover, leads to a relatively high rate of oxygen usage by the apparatus, it is now common for such apparatus to be provided with a gas mixing device in the form of an entrainment mixer that enables the apparatus to deliver either pure oxygen or oxygen diluted with entrained air.

BACKGROUND INFORMATION

Entrainment mixers are devices of commendably simple construction appropriate for incorporation in apparatus of this character. However, their simplicity also imposes constraints upon their controllability and performance under varying operational circumstances. GB-A-2174609 discusses these problems and discloses an arrangement that addresses these problems in a preferred type of resuscitation/ventilation apparatus. In summary, entrainment mixers that can provide a high mixing ratio deliver a gas mixture with flow rates and mixing ratios that are highly dependent upon the back pressure to which their output is exposed, whereas those that can only provide a low mixing ratio, typically in the range 1:1 to 2:1, are able to do so with relative stability of flow rate and mixing ratio over a wide back pressure range. However, as established in the art, resuscitation/ventilation apparatus having an entrainment mixer adapted to deliver a stable low ratio gas mixture has been arranged to deliver selectively a mixture at a single, fixed, ratio as an alternative to delivering 100% oxygen. Thus, typically, a resuscitation/ventilation apparatus with an entrainment mixer has been arranged to deliver a gas mixture at one oxygen concentration only, selected from 60%, 50% and 45%, as a single alternative to the delivery of 100% oxygen by the apparatus.

SUMMARY OF THE INVENTION

An object of the invention is to make provision for an entrainment mixer-equipped resuscitation/ventilation apparatus to deliver a gas mixture of steplessly variable oxygen concentration within a specific range of values, without compromising the simplicity of such apparatus and its operation. As will be explained, a resuscitator/ventilator equipped with an entrainment mixer in accordance with the invention may be adapted to deliver a gas mixture having an oxygen concentration of any selected value within a range extending from below 45% to 100%, or with any selected value within the range 21% to 70% or more, depending on the gas used to power the apparatus.

The invention is especially appropriate to neonatal and infant ventilators because these are often designed as pressure generators and hence can operate with a constant gas flow, enabling the entrainment mixer to maintain a precisely selected output gas composition that is for practical purposes independent of back pressure whilst employing the simplest physical arrangement of the invention. This is of particular advantage for this class of patient, for which the maintenance of a constant breathing gas composition can be of critical importance.

In existing resuscitator/ventilators having entrainment mixers as above discussed, 100% oxygen delivery is achieved either by bypassing the entrainment mixer or by supplying oxygen to the entrainment chamber of the mixer in place of the normal dilution air supply.

In accordance with the invention, resuscitation/ventilation apparatus having an entrainment mixer is characterised by provision for an adjustable flow of oxygen to be supplied to the entrained gas inlet port such that it raises the oxygen concentration of the entrained gas without affecting the rate of entrainment flow (i.e. the rate of air entrainment automatically decreases to compensate for the rate of oxygen addition).

If the primary entraining gas stream is oxygen as in the normal prior art arrangement, the delivery of a variable amount of oxygen to the entrainment gas taken by the mixer will enable the apparatus to output gas having an oxygen content ranging steplessly up to 100% from that (determined by the mixer geometry) corresponding to zero oxygen addition to the entrainment gas.

However, in accordance with a further feature of the invention, the primary entraining gas stream may be air so that the delivery of oxygen to the entrainment gas can serve to adjust the output gas oxygen concentration from 21% (standard atmosphere composition) up to about 70% or more, as determined by the entrainment mixer geometry.

In the case of apparatus operating at a constant output gas flow rate, the flow rate of oxygen supplied to the entrainment gas directly controls the output gas oxygen concentration and a simple needle valve control for the oxygen supply to the entrainment port of the mixer can be directly calibrated in terms of output gas composition. Where, however, the apparatus is intended to have an adjustable output flow rate, control of the oxygen supply to the entrainment port must be appropriately related to the primary gas stream flow control. In preferred embodiments of the invention, provision is made for simple and independent but coordinated control of both output flow rate and output gas mixture composition.

BRIEF DESCRIPTION OF THE DRAWINGS

The invention will be further explained by reference to the accompanying drawings in which.

DESCRIPTION OF THE PREFERRED EMBODIMENTS

Figure 1:
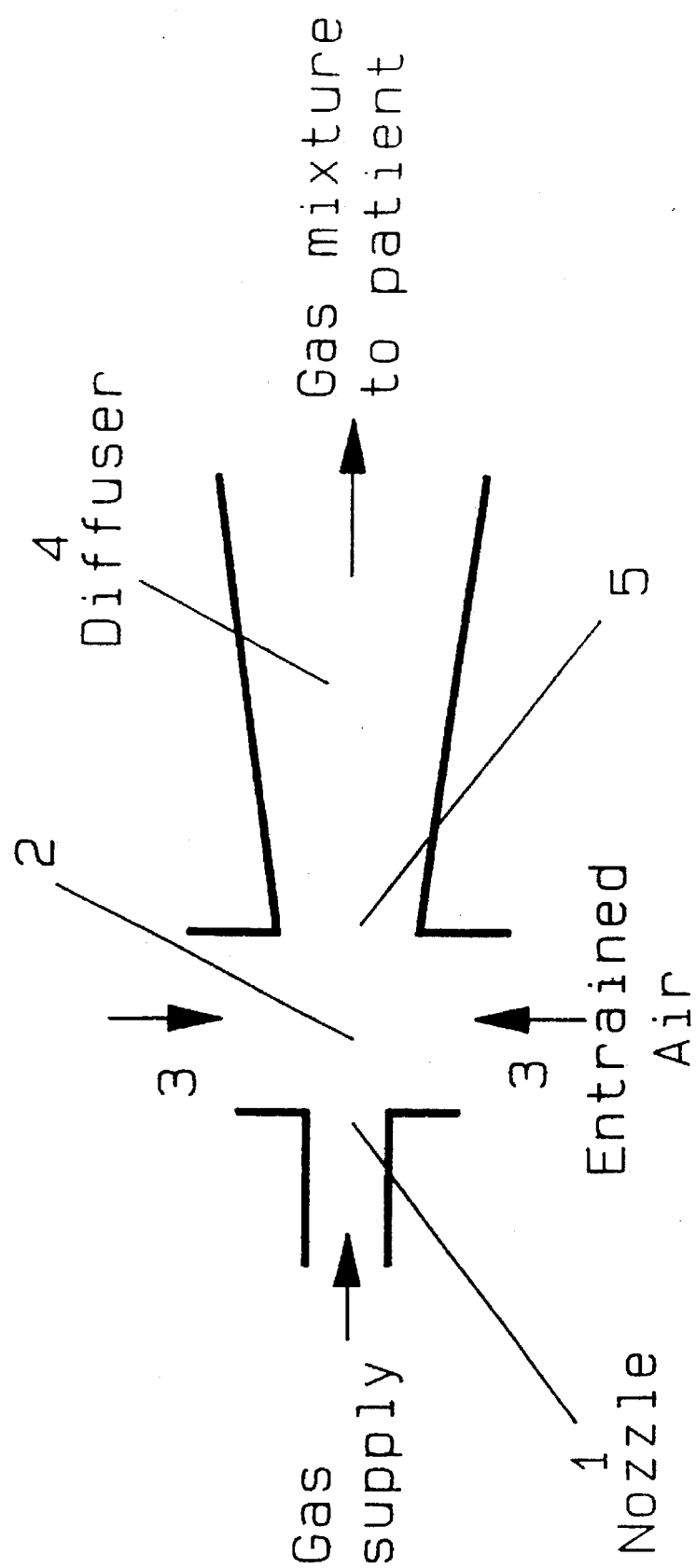
FIG. 1 is a schematic illustration of the principal features of an entrainment mixer.

Referring to the drawings, FIG. 1 shows the principal components of an entrainment gas mixer that comprises a nozzle 1 through which a primary or entraining gas stream is accelerated to flow across an entrainment chamber 2 having one or more lateral entrainment gas ports 3, to a pressure-recovery section in the form of a diffuser 4 of expanding cross-section. The geometry of the device and in particular the ratio between the areas of the nozzle 1 and the entry 5 to the diffuser 4 determines the ratio of entraining gas to entrained gas in the mixture delivered by the device. Because this geometry cannot be easily varied in a stepless manner, all such devices have in practice used a fixed geometry designed to produce a suitable, fixed, mixture ratio. As applied to resuscitation/ventilation apparatus, the primary or entraining gas supplied to the nozzle 1 is usually oxygen, delivered in suitably timed pulses from a pressurized oxygen source. The generation of such pulses is usually and most conveniently accomplished by the use of a pneumatic oscillator, for instance as disclosed in EP-A-0342883. The entrainment ports 3 are typically open to ambient atmosphere, directly or via a non-return valve, to enable the entrainment of air by the entraining oxygen stream. The diffuser 4 may be connected to a patient valve and thence to an oronasal mask or to an intratracheal tube. For certain applications, the diffuser 4 may be constructed in accordance with the disclosure of GB-A-2174760 to maintain effective pressure recovery as the gas flow rate changes during the inflation/inhalation phase of a ventilation cycle.

Typically, entrainment mixer geometries have been used such as to provide a gas mixture of 45%, 50% or 60% oxygen by volume.

Usually provision is made for delivery of 100% oxygen as an alternative to the fixed ratio gas mixture. This may be accomplished by bypassing the entrainment mixer altogether or by arranging for the oxygen supply to be delivered also to the entrainment ports so as to replace air as the entrained gas.

Figure 2A:
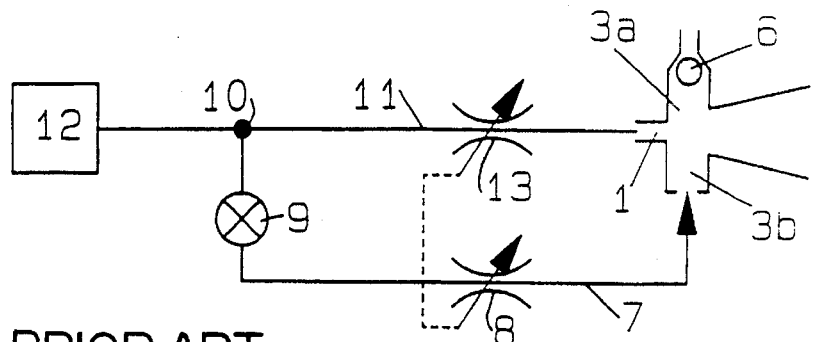
FIG. 2a is a schematic illustration of one prior art arrangement of an entrainment mixer in a resuscitation/ventilation apparatus.
Figure 3:
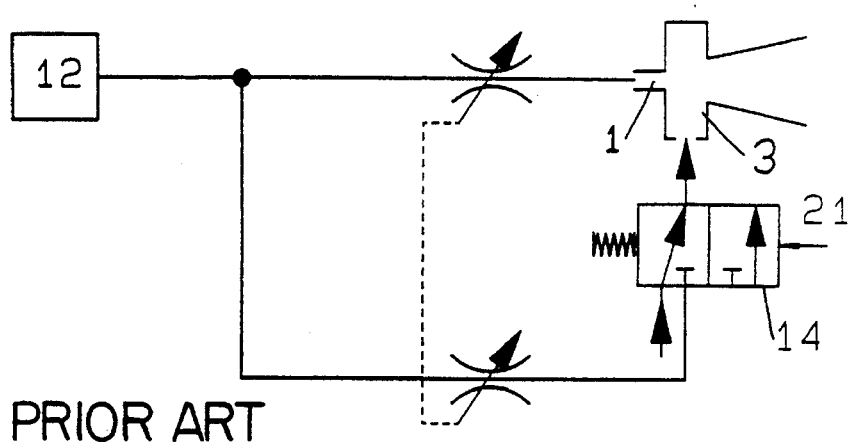
FIG. 3 schematically illustrates another prior art arrangement.
Figure 4A:
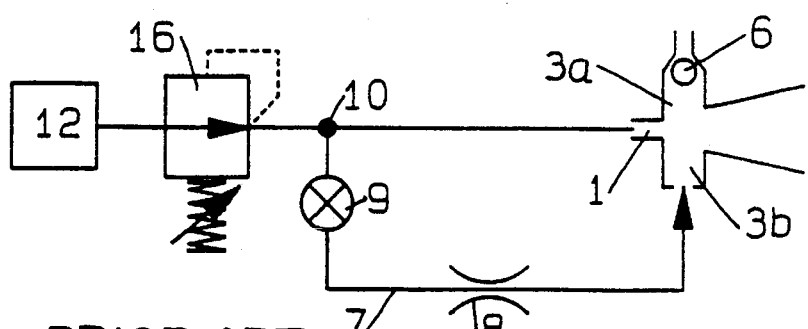
FIG. 4a illustrates the principles of a third prior art arrangement and FIG. 4b illustrates the modification thereof in accordance with the invention.

FIGS. 2a, 3 and 4a illustrate typical prior art arrangements by which 100% oxygen delivery is accomplished by the supply of oxygen to the entrainment ports of the mixer. Thus, FIG. 2a illustrates an arrangement in which one entrainment port 3a is connected to ambient atmosphere via a non-return valve 6 while another entrainment port 3b is connected to a line 7 extending via a restrictor 8 and an on/off valve 9 to a connection 10 in an oxygen supply line 11 extending from an oxygen pulse source 12 to the nozzle 1 of the entrainment mixer. In between connection 10 and nozzle 1, the line 11 includes a restrictor 13 that is adjustable for controlling the oxygen flow to the nozzle 1. The restrictor 13 is coupled to restrictor 8 so that an adjustment of restrictor 13 correspondingly adjusts restrictor 8 to provide to entrainment port 3b the appropriate amount of oxygen, when valve 9 is open, to be entrained by the oxygen stream from nozzle 1 without air dilution, when 100% oxygen delivery is required.

FIG. 3 shows an arrangement equivalent to that of FIG. 2a but in which the on/off valve 9 is replaced by a relay valve 14 connected to the entrainment ports 3 and switchable to open a connection with line 7 when required, by application of pilot pressure at its port 21. At other times the valve 14 connects ambient atmosphere to the entrainment ports 3.

FIG. 4a illustrates an arrangement in which a pressure regulator 16 is interposed between source 12 and connection 10 to cause oxygen to be delivered at a regulated pressure to nozzle 1, and also to line 7 when valve 9 is open. In this arrangement, restrictor 8 is of fixed value. Adjustment of the regulated pressure delivered by regulator 16 controls the flow without affecting the relationship between primary oxygen flow and entrainment oxygen flow. In known applications of this arrangement the regulator 16 is adjusted by means responsive to sensed output flow so as to maintain a constant output flow.

Figure 2B:
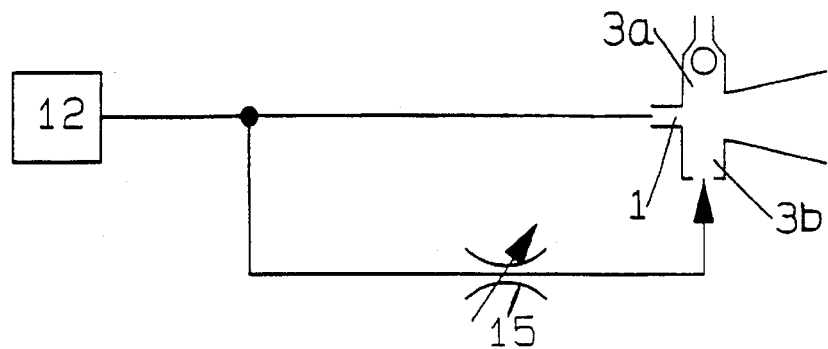
FIG. 2b illustrates modification of the arrangement of FIG. 2a in accordance with the invention.
Figure 4B:
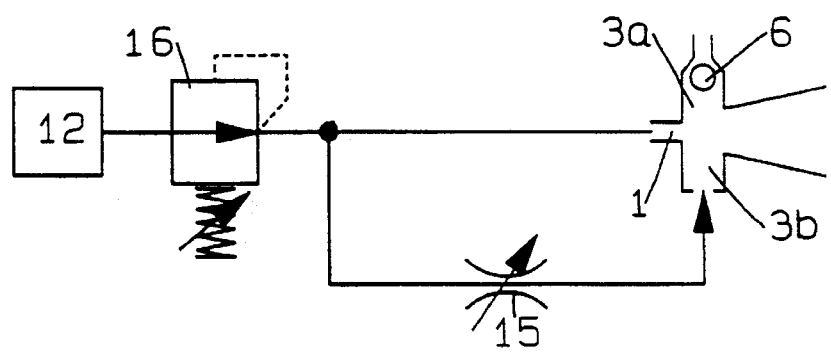

In accordance with the invention, the arrangements of FIGS. 2a and 4a may be modified as shown in FIGS. 2b and 4b respectively. In the case of the arrangement of FIG. 2a, the modification illustrated in FIG. 2b consists in omission of the on/off valve 9 and in substitution of an independently adjustable restrictor 15 for the restrictor 8, to provide oxygen flows to entrainment port 3b that may be steplessly adjusted, independently of the primary flow to nozzle 1, from the value appropriate for obtaining 100% oxygen output from diffuser 4, down to zero, when the geometry of the mixer determines the minimum output gas oxygen concentration, it being understood that when oxygen flow to the port 3b is less than that required for 100% oxygen output, the entrainment action will cause air to be drawn through valve 6 to port 3a for entrainment in the primary oxygen stream along with such oxygen as is concurrently being admitted via port 3b. However, as it is not possible to calibrate this device directly in terms of output gas oxygen concentration for a ventilator providing variable output flow rates, this arrangement is only suitable for constant flow ventilators. For such applications, the variable restrictor 13 of FIG. 2a is replaced by a fixed restriction of the primary flow nozzle.

As previously mentioned, neonatal or infant ventilators commonly operate as a pressure generator arranged to supply gas at a constant flow rate to a downstream patient connection, excess gas passing through a pressure relief valve. Because of the low flow rates involved (c.10 liters/minute as compared with c.60 liters/minute for adult ventilation), the gas losses resulting from constant pressure/constant flow operation are operationally acceptable. Such losses occur not only through the relief valve but also through the uncuffed endotracheal tube usually used for such applications. The arrangement of FIG. 2b is thus especially suitable for neonatal and infant use.

The calibration problems of the arrangement of FIG. 2b are avoided by modification of the arrangement of FIG. 4a in accordance with the invention, as illustrated in FIG. 4b. This modification involves elimination of the on/off valve 9 and the substitution of an adjustable restrictor 15 for the fixed restrictor 8 of FIG. 4a. Thus the arrangement of FIG. 4b provides for flow rate adjustment by adjustment of the regulator 16 and independent adjustment of the output gas oxygen concentration by adjustment of the restrictor 15. However, by omitting provision for adjustment of the pressure regulator 16, a ventilator as illustrated in FIG. 4b can also be configured as a constant pressure generator for e.g. neonatal or infant use as above described in relation to FIG. 2b.

Thus, with the arrangement shown in FIG. 4b, and irrespective of the regulated pressure set by regulator 16, the setting of the adjustable restrictor 15 will directly determine the oxygen content of the output gas and the control for the restrictor 15 may be calibrated accordingly.

Arrangements such as illustrated in FIGS. 2b and 4b enable a resuscitation/ventilation apparatus operating from a compressed oxygen source as described to deliver breathable gas pulses having oxygen contents ranging from 100% steplessly down to 45% or less by suitable choice of fixed geometry for the entrainment mixer.

However, in each case by substituting for pulsed oxygen source 12 a source of compressed air that is delivered pulsewise to the nozzle 1 and by supplying oxygen separately to line 7, a resuscitation/ventilation apparatus may be arranged to deliver breathable gas having an oxygen content ranging from 21% (air with no added oxygen) up to about 70% or more as determined by the fixed geometry of the entrainment mixer.

Whereas in the arrangements of FIGS. 2, 3 and 4, the oxygen supply to line 7 derives directly from the pulsed output of source 12 in line 11. (in FIG. 4 from the output of the pressure regulator 16), an alternative arrangement would utilise a relay valve connecting line 7 to a discrete oxygen source, the relay valve being actuated by the pressure pulses in line 11. Such an arrangement, which also overcomes the calibration problems of the arrangement of FIG. 2b, would be appropriate also to control the supply of oxygen to line 7 for the described substitution of a compressed air pulse source for the oxygen source 12.

Figure 5:
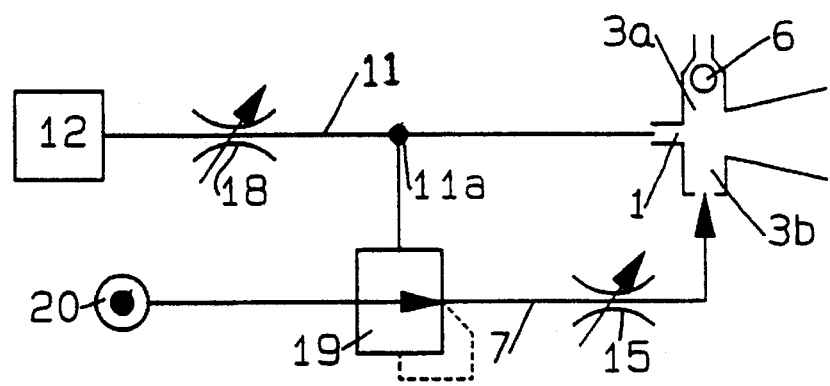
FIG. 5 illustrates a preferred embodiment of the invention.

FIG. 5 illustrates an embodiment of an arrangement with a discrete oxygen source. In this arrangement, the pulsed source of primary or entraining gas is shown at 12 and feeds the nozzle 1 of the entrainment mixer via line 11 and a variable restrictor 18 that serves to adjust the primary gas flow rate. Downstream of the restrictor 18, a servo connection 11a extends from line 11 to a relay valve 19 that controls the flow of oxygen from a discrete source 20 to line 7 that is connected to entrainment port 3b via an adjustable restrictor 15. The relay valve 19 is arranged to close in the absence of pressure at the servo connection 11a, so that the pressure pulses in line 11 cause corresponding and coordinated flow pulses of oxygen to the entrainment port 3b. The primary gas provided by source 12 may be oxygen or air, depending upon the oxygen concentration range required for the output gas mixture.

Because relay valve 19 follows the pressure profile of the primary gas supplied to the entrainment mixer nozzle, the pulses of oxygen delivered by the valve 19 to the entrainment port 3b will be proportional in volume to the primary gas pulses, so that an adjustment of primary gas flow rate by adjustment of restrictor 18 will result in a corresponding adjustment of the oxygen flow rate in line 7, for any given setting of restrictor 15. Accordingly, having set restrictor 15 to provide a required output gas mixture oxygen concentration at one flow rate (tidal volume or constant pressure, as determined by the downstream configuration) the flow rate may thereafter be adjusted by adjustment of restrictor 18 without affecting the output gas mixture oxygen concentration.

A further variant, not shown, corresponds to that shown in FIG. 5 with the variable restrictor 18 omitted, that is to say having a fixed restrictor, which may simply be the outlet of the pulsed primary source 12, in place of the variable restrictor. This variant constitutes a constant flow device in which the oxygen concentration of the gas supplied to the patient can be varied. With the arrangement of FIG. 5 and the variant just described, if the primary gas provided by source 12 is oxygen, the oxygen concentration of the gas supplied to the patient can be varied up to 100% by adjustment of the variable restrictor 15, (from a value determined by the mixer geometry) and, if the primary gas provided by source 12 is air, the oxygen concentration of the gas supplied to the patient can be varied down to 21% by adjustment of restrictor 15. A simple changeover valve may be provided for changing the gas supplied by source 12 from air to oxygen or vice versa.

I claim:

1. Resuscitation/ventilation apparatus including:
   (a) an entrainment mixer comprising an entrainment chamber, a diffuser extending from the entrainment chamber and expanding in cross-section from the entrainment chamber, a nozzle opening into the entrainment chamber and directed across the entrainment chamber towards the diffuser, a first entrainment gas port communicating laterally with the entrainment chamber and communicating with atmosphere, and a second entrainment gas port communicating laterally with the entrainment chamber;
   (b) a source of oxygen under pressure;
   (c) a primary gas line for supplying oxygen from said source of oxygen under pressure to said nozzle to issue in a stream across the entrainment chamber into the diffuser;
   (d) an oxygen supply line extending to said second entrainment gas port;
   (e) means communicating said source of oxygen under pressure with said oxygen supply line; and
   (f) means in said oxygen supply line for steplessly adjusting the flow of oxygen from said oxygen source to said second gas port independently of the flow of oxygen from said oxygen source through said primary gas line.

2. Apparatus according to claim 1, including a pressure regulating valve having an outlet, and further having an inlet connected with said source of oxygen under pressure, said primary gas line and said oxygen supply line being connected with said outlet of said pressure regulating valve.

3. Apparatus according to claim 1, wherein said source of oxygen under pressure is operable to deliver the oxygen gas pulsewise to the nozzle and to said oxygen supply line.

4. Resuscitation/ventilation apparatus including:
   (a) an entrainment mixer comprising an entrainment chamber, a diffuser extending from the entrainment chamber and expanding in cross-section from the entrainment chamber, a nozzle opening into the entrainment chamber and directed across the entrainment chamber towards the diffuser, a first entrainment gas port communicating laterally with the entrainment chamber and communicating with atmosphere, and a second entrainment gas port communicating laterally with the entrainment chamber;
   (b) a source of primary gas;
   (c) means for supplying primary gas from said source of primary gas to said nozzle to issue in a stream across the entrainment chamber into the diffuser;
   (d) a source of oxygen under pressure;
   (e) an oxygen supply line extending between said source of oxygen under pressure and said second entrainment gas port; and (f) means in said oxygen supply line for steplessly adjusting the flow of oxygen from said oxygen source to said second gas port.

5. Apparatus according to claim 4, wherein said source of primary gas is a source of air under pressure.

6. Apparatus according to claim 4, wherein said means for supplying primary gas from said source of primary gas to said nozzle is operable to deliver the primary gas pulsewise to the nozzle.

7. Apparatus according to claim 6, including a relay valve controlling the supply of oxygen to said oxygen supply line from said source of oxygen under pressure, said relay valve communicating with said means for supplying said primary gas to said nozzle whereby said relay valve is caused to open during the pulses of primary gas supplied to the nozzle.

* * * * *